United States Patent [19]

Girijavallabhan et al.

[11] Patent Number: 4,587,241
[45] Date of Patent: May 6, 1986

[54] HETEROCYCLIC SUBSTITUTED PENEMS

[75] Inventors: Viyyoor M. Girijavallabhan, Parsippany; Ashit K. Ganguly, Upper Montclair; Richard W. Versace, Ringwood, all of N.J.

[73] Assignee: Schering Corporation, Kenilworth, N.J.

[21] Appl. No.: 590,086

[22] Filed: Mar. 16, 1984

Related U.S. Application Data

[63] Continuation-in-part of Ser. No. 555,738, Nov. 28, 1983, abandoned.

[51] Int. Cl.$^4$ ................ C07D 499/00; A61K 31/425
[52] U.S. Cl. ............................ 514/192; 260/245.2 R; 260/239 A
[58] Field of Search ................ 260/245.2 R; 514/192

[56] References Cited

U.S. PATENT DOCUMENTS 4,260,618  4/1981  Christensen et al. ........ 260/245.2 R
4,431,654  2/1984  Girijavallabhan ........... 260/245.2 R

FOREIGN PATENT DOCUMENTS 2013674A  8/1979  United Kingdom .

*Primary Examiner*—Nicholas S. Rizzo
*Attorney, Agent, or Firm*—Gerald S. Rosen; Anita W. Magatti

[57] ABSTRACT

There is disclosed 2-(arylalkyl-heterocyclylalkylthio)-penems having long serum half-lives and their uses as antibacterial agents.

14 Claims, No Drawings

HETEROCYCLIC SUBSTITUTED PENEMS

RELATED APPLICATIONS

This application is a continuation-in-part of U.S. patent application Ser. No. 555,738, filed Nov. 28, 1983, now abandoned.

BACKGROUND OF THE INVENTION

This invention relates to 2-(acylalkyl-heterocycloalkylthio)penems and their pharmaceutically acceptable salts and esters, which compounds possess potent antibacterial activity and advantageous long serum half-lives.

There is a continuing need for new antibacterial agents because continued extensive use of effective antibacterials gives rise to resistant strains of pathogens. Additionally, a need exists for reducing dosages and administration frequency. We have discovered that this can be accomplished by the compounds of this invention since they have long serum half-lives and, consequently, a longer period of action.

SUMMARY OF THE INVENTION

The novel penem compounds of this invention are represented by the formula

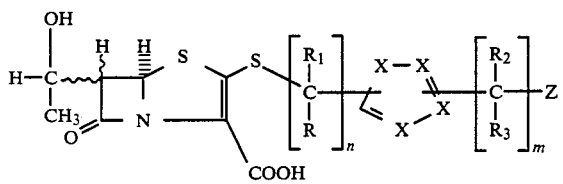

and pharmaceutically acceptable salts and esters thereof in racemic or optically active forms wherein n is 1, 2 or 3; m is 1, 2 or 3;

Z represents —COOH, —SO$_3$H,

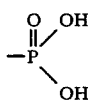

or alkali metal salts thereof;

R, R$_1$, R$_2$ and R$_3$ independently represent hydrogen, lower alkyl, hydroxy lower alkyl, amino lower alkyl carboxy lower alkyl, thio lower alkyl, lower alkoxy lower alkyl, carbonylamino lower alkyl, aminocarbonyl lower alkyl, cyano lower alkyl, fluoro lower alkyl, carbamoyloxy lower alkyl, or sulfamoyloxy, with the proviso that when m is 2 or 3, R, R$_1$, R$_2$ and R$_3$ independently additionally represent hydroxy, amino, cyano, fluoro, carbamoyloxy, carbonylamino or —SO$_3$H;

each X independently represents —CH—, —N—, —S— or —O— with the proviso that at least one X is —N—.

Heterocyclic moieties within the scope of this invention are pyrrole, imidazole, pyrazole, triazoles, tetrazoles, thiadiazoles, thiazole, oxazole, oxydiazoles, isoxazole and isothiazole. These heterocyclics include all the isomeric forms, e.g., 1,2,3 triazole, 1,2,4-triazole, 1,2,3-oxydiazole, 1,2,3,4-tetrazole, 1,3,4-thiadiazole and the like. The heterocyclic moiety can be attached to the penem molecule by a ring carbon or nitrogen.

Preferred heterocyclic moieties are imidazole, 1,2,4-triazole, 1,2,3-triazole and 1,2,3,4-tetrazole.

Preferred compounds of formula I are those in which n is 1 or 2; m is 1; R, R$_1$, R$_2$ and R$_3$ are independently hydrogen or lower alkyl; Z is —SO$_3$H or —COOH and two non-adjacent X's are —N—.

Most preferred are those compounds in which n is 1, m is 1, R$_1$ and R$_3$ are each hydrogen, R and R$_2$ are independently hydrogen or a lower alkyl, Z is —SO$_3$H and the heterocyclic ring is a 2-imidazole.

The term "lower alkyl" as used herein means straight and branched chain alkyl groups of 1 to 6 carbon atoms, e.g., methyl, ethyl, propyl, i-propyl, butyl, t-butyl, pentyl, neopentyl, hexyl and the like. Similarly, "lower alkoxy" means straight or branched chain alkoxy groups having 1 to 6 carbon atoms, e.g. methoxy, ethoxy, propoxy, i-propoxy, butoxy, i-butoxy, neopentoxy, pentoxy and the like.

As used herein, "pharmaceutically acceptable salts" means alkali metal salts such as sodium and potassium salts; alkaline earth metal salts such as calcium, magnesium and aluminum salts; amine salts formed from a wide variety of suitable organic amines, i.e., aliphatic, cycloaliphatic, (cyloaliphatic)aliphatic or araliphatic primary, secondary or tertiary mono-, di- or polyamines, or heterocyclic bases, e.g., salts derived from triethylamine, 2-hydroxyethylamine, di-(2-hydroxyethyl)amine, tri-(2-hydroxyethyl)amine, 4-aminobenzoic acid-2diethylaminoethyl ester, 1-ethylpiperidine, bicyclohexylamine, N,N'-dibenzylethylenediamine, pyridine, collidine, quinoline, procaine, dibenzylamine, 1-ephenamine and N-alkylpiperidine. Acid addition salts formed from mineral acids such as hydrochloric, hydrobromic, hydroiodic, phosphoric or sulfuric acids, or formed from organic carboxylic or sulfonic acids such as trifluoroacetic, para-toluene sulfonic, maleic, acetic, citric, oxalic, succinic, benzoic, tartaric, fumaric, mandelic, ascorbic and malic acids. The compounds of this invention contain a 3-carboxylic group and a basic group (the heterocyclic group) which form an inner salt, i.e., a Zwitterion.

"Pharmaceutically acceptable esters" means physiologically cleavable esters, i.e., metabolizable esters known in the penicillin, cephalosporin and penem arts to be easily cleaved within the body to the parent acid. Examples of such esters are indanyl, phthalidyl, methoxymethyl, glycyloxymethyl, phenylglycyloxymethyl, thienylglycyloxymethyl, acetoxymethyl and pivaloyloxymethyl.

Preparation of the foregoing salts and esters may be carried out according to conventional procedures for forming salts of beta-lactams such as penicillins, cephalosporins and penems. Salts of the compound can be formed, for example, by treating with metal compounds such as alkali metal salts of suitable carboxylic acids, or with ammonia or a suitable organic amine, wherein preferably stoichiometric amounts or only a small-excess of the salt-forming agent is used. Acid addition salts of the compound are obtained in the usual manner, for example, by treating with an acid or a suitable anion exchange reagent. Inner salts of the compounds of formula I, i.e., a zwitterion, may be formed by neutralizing salts such as acid addition salts to the isoelectric point. The esters are preferable in a manner analogous to the preparation of the corresponding esters of penicillins and cephalosporins.

Salts may be converted in the usual manner into the free carboxy compounds.

Compounds of this invention possess 3 or more asymmetric carbon atoms indicated in the partial formula I(a) below at the 5,6,8 and 2' to 4'-position carbon atoms

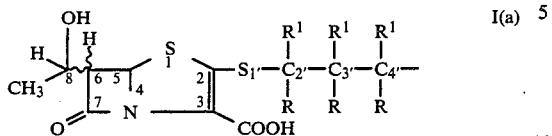

At the 5,6 and 8 positions, compounds of the invention may possess 5R, 6S, 8R or 5R, 6R, 8S stereochemistry at those chiral atoms. The preferred absolute stereochemistry for the compounds of the present invention at those positions is 5R, 6S, 8R.

Compounds of this invention wherein R and $R^1$ on the carbon atom are different will have additional asymmetric carbon atom(s) as shown in formula I(a) at the 2' to 4' positions. All the possible resulting stereoisomers are included herein.

DETAILED DESCRIPTION

The compounds of this invention display activity against gram-negative and gram-positive bacteria in standard microbiological assays. When tested in preliminary pharmokinetic tests in mice, penems generally have a serum half-life of between 5 and 10 minutes with about 7 minutes being the average. The compounds of this invention in the same tests have a longer serum half-life, generally on the order of at least twice as long, on the average.

The compounds of this invention and their metabolites have little or no unpleasant odor.

When tested in standardized microbiological assays, the compounds of this invention are active against such gram-positive organisms as *Staphylococcus epidermis* and *Bacillus subtilis*, and such gram-negative organisms as *E. coli* and Salmonella, at test levels of 0.01 to 1.0 micrograms/ml. Additionally, they show activity against organisms which produce beta-lactamases, e.g., penicillinase and cephalosporinase, indicating a stability toward these enzymes.

As antibacterial agents, the compounds of this invention are conventionally formulated for oral, parenteral, topical and transdermal use. Thus, this invention includes within its scope pharmaceutical compositions comprising the compounds of this invention in admixture with a pharmaceutically acceptable carrier therefor. In addition, the present invention also provides a method of treating bacterial infections in animals, particularly warm-blooded animals, including humans, having a susceptible bacterial infection which comprises administering to said animal an antibacterial effective amount of a compound of this invention, or a pharmaceutical composition thereof. In the foregoing compositions, the compounds of this invention can be used as the sole active antibacterial agent or in combination with other antibacterial agents and/or enzyme inhibitors.

For oral administration, the compounds of this invention are typically formulated in the form of tablets, capsules, elixirs, or the like. For parenteral administration, they may be formulated into solutions or suspensions.

Typical topical formulations are those such as lotions, creams, ointments, sprays, and mechanical delivery devices, e.g., transdermal. Parenteral administration is preferred. Typical pharmaceutically acceptable carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinyl pyrrolidone; polyvinyl alcohol; stearic acid; alkaline earth metal stearates such as magnesium stearate; vegetable oils such as peanut oil, cottonseed oil, sesame oil, olive oil and corn oil; non-ionic, cationic and anionic surfactants; ethylene glycol polymers; betacyclodextran; fatty alcohols; hydrolyzed cereal solids; water; polyalkylene gylcols; gums; and petrolatum; as well as other non-toxic compatible fillers, binders, disintegrants and lubricants commonly used in pharmaceutical formulations. The compositions may also contain preservatives, aerosol propellants and coloring, thickening, suspending, dispensing, emulsifying, wetting, stabilizing and buffering agents.

The dosage of the compounds of this invention which is administered is dependent, in the judgement of the attending clinician, upon a variety of factors, e.g., the age and weight of the individual being treated, the mode of administration, and the type and severity of the bacterial infection being prevented or reduced. Typically, the dosage administered per day will be in the range of from about 1 to 250 mg/kg and preferably from about 5 to 20 mg/kg in divided dosages. Typically, the dosage will be administered in dosage units containing convenient amounts, for example, 125, 250 or 500 mg of active ingredient combined with a suitable physiologically acceptable carrier or diluent.

The compounds of this invention are prepared by the processes disclosed in applicants assignees copending U.S. patent application Ser. No. 549,535 entitled "Process for the Production of Penems" filed Nov. 7, 1983. The processes disclosed therein are preferred over other known suitable processes for preparing penems.

The process designated as process A in the aforesaid patent application comprises (a) reaction of an azetidinone of the formula

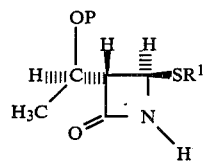

II wherein P is a removable hydroxy protecting group or hydrogen; and $R^1$ is a sulfur protecting group selected from triphenylmethyl, diphenylmethyl, 2-pyranyl, or lower alkyl carbonyl; with a compound of the formula IIIa and IIIb.

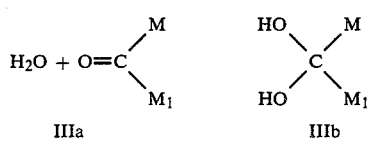

wherein M and $M_1$ are independently $-COOCH_2CH_2R^2$ or $-COOCH_2CH=CH_2$; $R^2$ is lower mono, di or tri alkyl silyl, e.g., trimethylsilyl, or t-butyldiphenylsilyl, cyano or a sulfone of the formula —SO₂-aryl; to form the intermediate of the formula IV

IV wherein P, R¹, M and M₁ are as hereinabove defined;

(b) treatment of the compound of formula IV with a chlorinating agent to form the following compound of formula V

V wherein P, R¹, M and M₁ are as defined hereinabove;

(c) treatment of the compound of formula V with a stoichiometric excess of elemental zinc in a strong acid such as hydrochloric acid to effect removal of the chlorine and the removable sulfur and hydroxy protecting groups, and, if a removable hydroxy protecting group is utilized which is not removable with zinc, subsequent removal of said hydroxy protecting group, producing a compound of formula VI

VI wherein M and M₁ are as hereinabove defined;

(d) treatment of the compound of formula VI with a hydroxy protecting group to form the compound of formula VI(a)

VI(a)

wherein M and M₁ are as defined hereinabove and P is a hydroxy protecting group as defined hereinabove;

(e) reaction of the compound of formula VI or VI(a) with a thiocarbonyl compound of formula VII $$S=C(-Y)_2 \quad \text{VII}$$

wherein Y is a leaving group; to form a compound of formula VIII

VIII wherein P, M and M₁ are as hereinabove defined;

(f) treatment of the compound of formula VIII wherein P is a hydroxy protecting group with an aqueous acid solution to deprotect the hydroxy group to form a compound of formula VIII(a)

VIII(a)

wherein M and M₁ are as hereinabove defined;

In an alternative procedure, compounds of formula VIII(a) can be prepared from compounds of formula V by eliminating steps (d) and (f) (i.e. the protection and subsequent deprotection of the hydroxyl group at the C-8 position).

(g) treatment of the compound of formula VIII(a) with a fluoride ion (when M is —COOCH₂CH₂R² and R² is trimethyl silyl only one equivalent of fluoride need be used) to form the compound of formula IX(a) which is tautomeric with formula IX(b)

IX(a)     IX(b)

wherein M is as defined above.

(h) reaction of the tautomer of formulas IX(a) and IX(b) with a compound of formula XII

XII wherein L' is a leaving group such as trifluoromethansulfonyl (triflate), bromine, or chlorine, L" is Z or Z protected with a group such as allyl; R, R₁, X, R₂, R₃, m, n and Z are as hereinabove defined, to form a compound of the formula XIII

XIII wherein R, $R_1$, $R_2$, $R_3$, X, m, M, L" and n are as hereinabove defined.

(i) treatment of a compound of formula XIII under catalytic conditions when M is —COOCH$_2$CH=CH$_2$ to remove the allyl protecting group in the presence of an alkali base (if the product is a zwitterion, deprotection requires only the catalyst and any mild nucleophile, e.g., H$_2$O, alcohol, etc.) or if M is —COOCH$_2$CH$_2$R$^2$, treating the compound of formula XIII with one equivalent of fluoride ion to form the compounds of formula I.

The preferred process for producing the compounds of this invention is referred to as Process C in the aforementioned patent application and comprises the steps of (a) reaction of the azetidinone of formula II in which P is hydrogen as in the following formula II(a)

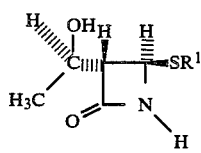
II(a)

wherein R$^1$ is a sulfur protecting group selected from triphenylmethyl, diphenylmethyl, 2-pyranyl, or lower alkyl carbonyl; with an α-substituted allyl acetate of formula XIV

WCH$_2$CO$_2$CH$_2$CH=CH$_2$     XIV wherein W is a leaving group; to form the intermediate of the formula XV

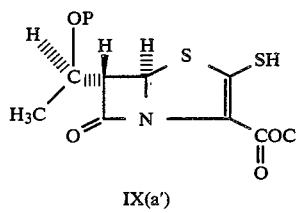
XV wherein R$^1$ is as defined hereinabove.

(b) treatment of the compound of formula XV with a stoichiometric excess of elemental zinc in a strong acid to deprotect the sulfur and form the compound of formula XVI

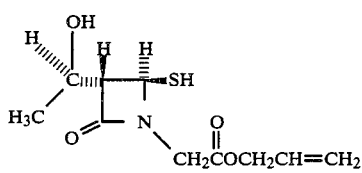
XVI (c) treatment of the compound for formula XVI with a hydroxy protecting group to form the compound of formula XVI(a)

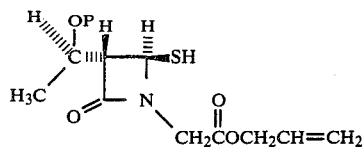
XVI(a)

wherein P is a hydroxy protecting group as hereinabove defined;

(d) reaction of the compound of formula XVI or XVI(a) with a thiocarbonyl compound of formula VII

S=C(—Y)$_2$     VII wherein Y is a leaving group to form a compound of formula XVII

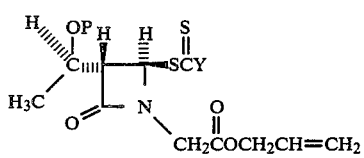
XVII wherein Y and P are as hereinabove defined;

(e) treatment of compound XVII with a non-nucleophilic strong base to form a compound of formula IX(a') which is tautomeric with formula IX(b')

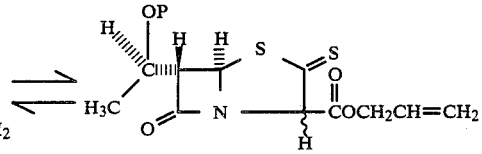

IX(a')            IX(b')

wherein P is as hereinabove defined;

(f) treatment of the tautomer of formulas IX(a') and IX(b') under conditions which effect removal of the hydroxy protecting group when P is a hydroxy protecting group.

Following steps (h) and (i) of Process A as applied to the tautomer of formulas IX(a') and IX(b') yields compounds of formula I.

In the most preferred embodiment the α-substituted allyl acetate of formula XIV is added to the azetidinone of formula II(a) to form the intermediate of formula XV. The intermediate of formula XV is then utilized directly in steps (b), (c) and (d) which are conducted sequentially without isolation of any intermediates.

Likewise steps (e) and (f) are preferably conducted sequentially without the necessity of isolating any intermediates.

Step (a) involves the reaction of an azetidinone of formula II(a) at 15°–30° C. in the presence of an acid acceptor with an α-substituted allyl acetate of formula XIV to form the compound of formula XV. Preferred W leaving groups in the compound of formula XIV include tosyl, mesyl, chloro, bromo, iodo, and trifluoromethanesulfonyl. Particularly preferred W leaving groups are iodo and bromo.

Where the solvent utilized is also an acid acceptor, for instance, pyridine, no additional reagent is utilized. Alternatively, an organic solvent such as acetonitrile may be employed. In these cases, a separate acid acceptor, organic or inorganic must be added to the system. Preferably, the reaction is conducted in acetonitrile employing cesium carbonate or tetra alkyl ammonium hydroxide as the acid acceptor.

Step (b) involves the conversion of the compound of formula XV to the corresponding thiol of formula XVI by deprotecting the sulfur with a stoichiometric amount of elemental zinc in hydrochloric acid. Step (c) involves the protection of the 6-hydroxy substituent to form the compound of formula XVI(a) with the preferred protecting group being trimethylsilyl, whereas step (d) is that wherein a compound of formula XVI or XVI(a) is converted to a compound of formula XVII by addition of a thiocarbonyl reagent of formula VII wherein the Y leaving group is typically imidazolyl, chloro, bromo, or iodo.

In Step (b) typically, a polar solvent such as methylene chloride, methanol, ethanol, dimethylformamide (DMF), tetrahydrofuran, dimethylsulfoxide or acetonitrile is utilized. Water, or any proton source, adjusted by the addition of a strong acid, is added to enhance the activity of zinc. Typical temperatures range from $-15°$ C. to about room temperatures (about 25° C.) with a temperature of about 0° C. being preferred. The removable hydroxy and sulfur protecting groups used are preferably those which are removable by elemental zinc. In the event a removable hydroxy protecting group is used which is not removable by zinc, a separate removal step is conducted to remove the hydroxy protecting group by means well known in the $\beta$ lactam art. This separate removal step can be conducted immediately after this step (b) or at any other time in the process after step (b).

Step (c) involves the protection of the 8-hydroxy substituent if it had not been previously protected. Hydroxy protecting groups are well known in the beta lactam art. A particularly preferred reagent for this step is bis trimethylsilylacetamide which readily forms the trimethylsilyl protecting group at the 8-hydroxy moiety. Preferably step (c) is conducted directly upon the completion of step (b) without isolation of the thiol of formula XVI. Thus the inert solvent utilized, e.g. DMF, may be the same as the one used in step (b). Solvents such as chloroform, methylene chloride and the like may also be employed in step (c). Temperatures for the reaction of step (c) range from 0° C. to 30° C.

Step (d) is wherein the intermediate of formula XVI or XVI(a) is converted to the compound of formula XVII by reaction of the compound of formula XVI or XVI(a) with the thiocarbonyl reagent of formula VII. Typically, this step (d) is conducted directly upon the completion of step (c) without isolation of the intermediate of formula XVI or XVI(a). Thus, the solvent utilized may be the same as the one used in step (c). Temperatures for the reaction of step (d) range from about 10° C.–45° C., with room temperature (about 25° C.) being generally preferred. The thiocarbonyl reagent of formula VII has the following structure $$S=C(-Y)_2 \qquad \text{VII}$$

wherein Y is a leaving group. Typical of such leaving groups are chloro, bromo, iodo, imidazolyl or aryloxy such as naphthyloxy. Preferred are 1,1′-thiocarbonyldiimidazole or beta naphthyloxythiocarbonylchloride.

Step (e) involves the cyclization of the compound of formula XVII into the thione of formulas IX(a′) and IX(b′). The reaction is typically conducted in an anhydrous inert organic solvent such as tetrahydrofuran and the like. An essentially equimolar amount of a strong base such as lithium diisopropyl amide (LDA), lithium di(trimethylsilyl)amine and the like is added to the system to effect cyclization. Typically, the reaction is conducted at from $-50°$ to $-100°$ C. and preferably at $-70°$ C. and is generally complete from within 5 minutes to 24 hours.

Step (f) involves the removal of the 8-hydroxy protecting group in the compound of formulas IX(a′) and IX(b′) to form the compound of formulas IX(a) and IX(b).

Methods for the removal of this group are well known in the $\beta$-lactam art. Preferably, when the 8-hydroxy protecting group is trimethylsilyl, addition of a mild aqueous acid solution, such as acetic acid, to the same solution as is employed in step (e) effects removal.

The term "removable hydroxy protecting group" as used herein means any such group conventionally used for this purpose, with the only requirement being compatibility with the hydroxy substituent on the penems and removability utilizing elemental zinc or any other conventional agent for this purpose which will not adversely affect the penem structure. For the purpose of this invention, preferred hydroxy protecting groups include trichloroethoxycarbonyl, dimethyltributylsilyl, trimethylsilyloxycarbonyl and trimethylsilyl.

Step (h), is wherein the reaction of compounds of formulas IX(a) and IX(b) with compounds of formula XII is conducted in an inert atmosphere, such as nitrogen, in an organic solvent such as tetrahydrofuran (THF). The reaction is completed within 1 to 3 hours to yield allyl-2-(heterocycloalkylthio)-6-(1-hydroxyethyl)-penem-3-carboxylate compounds of formula XIII.

Removal of the allyl group in Step (i) to yield the compounds of formula I is effected by the addition of the above allyl ester to a solution containing palladium (zero) and an alkali alkylcarboxylate, carboxylic acid or aqueous carbonate. This is described by McCombie in U.S. Pat. No. 4,314,942 which is incorporated herein by reference. Under these conditions, the removal of the allyl group and formation of the alkali salt or the free acid of the compound occurs.

The compounds of formulas XII are prepared from known heterocyclic compounds by several reaction procedures which locate the

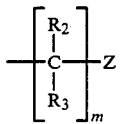

component at any desired location. The following reaction schemes show the preparations using imidazole starting materials for illustrative purposes since the reactions are equally applicable to all the heterocyclics within the scope of this invention.

Scheme I
Step (1)

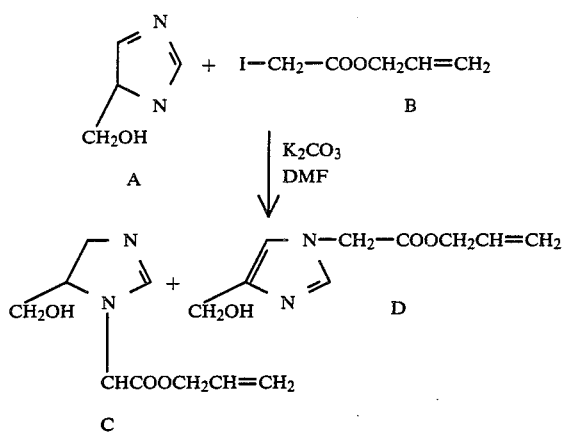

In step (1) the 2-hydroxymethyl imidazole is reacted with allyl-iodoacetate (B) in a basic medium to form isomeric compounds C and D. The isomers are separated by chromatography and treated separately in the subsequent steps to form compounds XII as follows

Step (2)

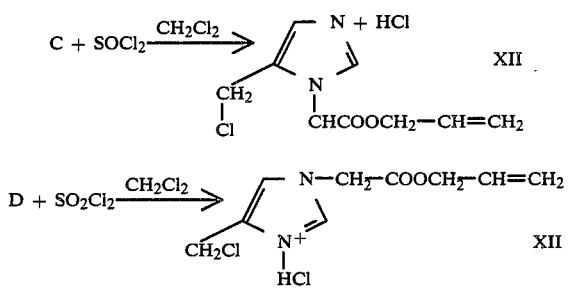

In step (2) the hydroxy is replaced by a halogen with thionyl chloride in an organic solvent to form compounds of formula XII. The compounds of formula I are formed from compounds XII by following steps (h) and (i) described hereinabove.

Scheme II
Step (1)

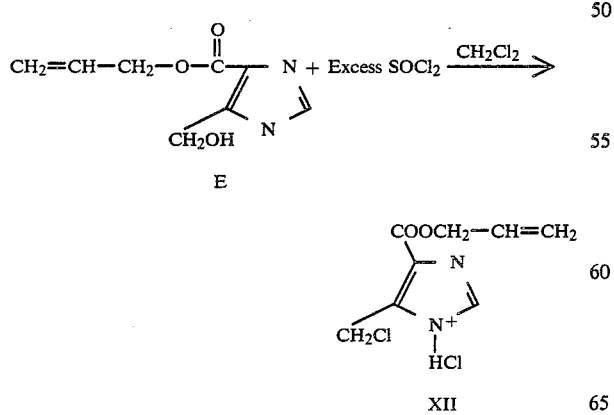

In step (1) the hydroxy group of compound E is replaced by a halogen by reaction with thionyl chloride in an organic solvent to form compound XII. Following the procedures of steps (h) and (i) described hereinabove compound XII is converted to compound of formula I.

Scheme III
Step (1)

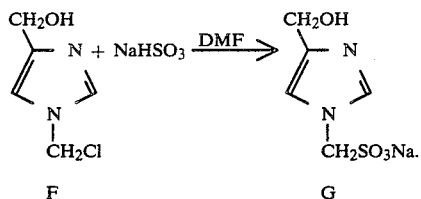

In step (1) compound F is sulfonated by reaction with sodium acid sulfate in an organic solvent to form compound G.

Step (2)

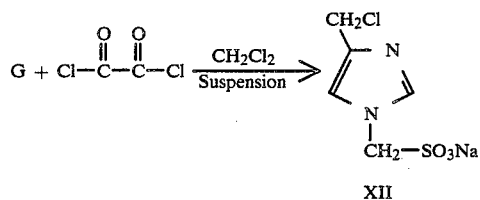

In step (2) the hydroxy of compound G is converted to a chlorine by reaction of oxalyl chloride suspended in an organic solvent to form a compound XII. Following the procedures of steps (h) and (i) described hereinabove, compound XII is converted to a compound of formula I.

Scheme IV
Step (1)

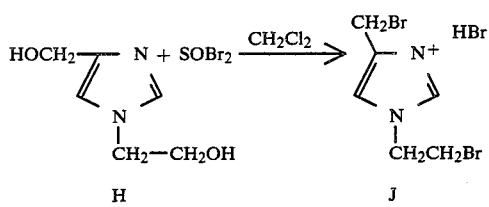

In step (1) the hydroxy groups of compound H are brominated by thionyl bromide in an organic solvent to give compound J.

Step (2)

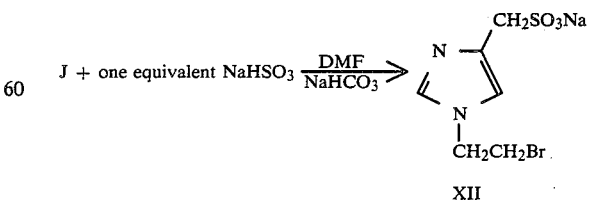

In step (2) the bromomethyl group of compound J is sulfonated with one equivalent of sodium acid sulfite in an organic solvent and sodium acid carbonate.

Following the procedures of steps (h) and (i) described hereinabove compound XII is converted to a compound of formula I.

Scheme V

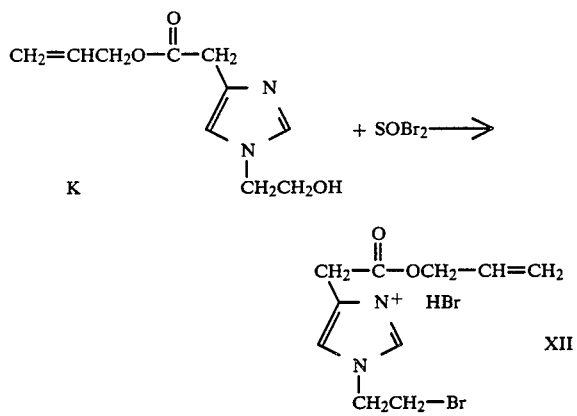

In Scheme V, the hydroxy group of compound K is converted to a bromine by reaction with thionyl bromide to give a compound of formula XII. Following the procedures of steps (h) and (i) described hereinabove the compound of formula XII is converted to a compound of formula I.

Using other heterocyclic compounds analogous to compounds A, E, F, H and K and following the above reaction schemes gives the analogous compounds of formula I. Examples of typical, representative suitable starting materials are the following:

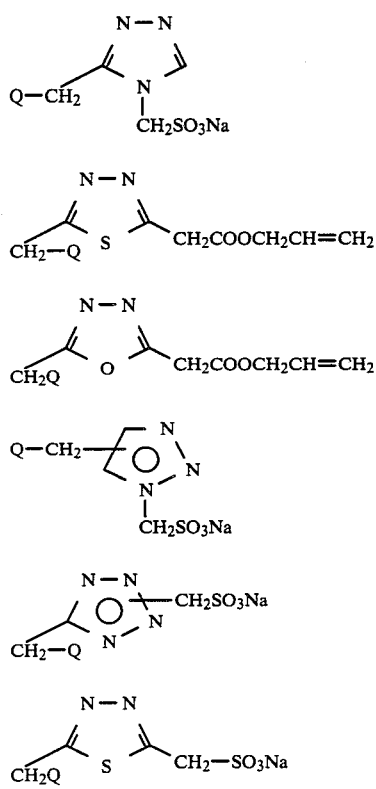

wherein Q is a leaving group.

An alternate process for producing compounds of formula I is the reaction of a 2-lower alkyl sulfinyl substituted penem of the formula K

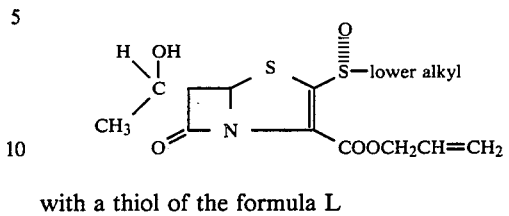

with a thiol of the formula L

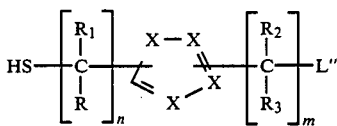

wherein R, $R_1$, $R_2$, $R_3$, L", n and m are as defined hereinabove.

Compound L is either a known compound or is prepared by known processes using known starting materials or analogous starting materials prepared by processes analogous to those known in the art.

Scheme VI illustrates the preparation of compound L is which L" is —$SO_3H$.

Step (1)

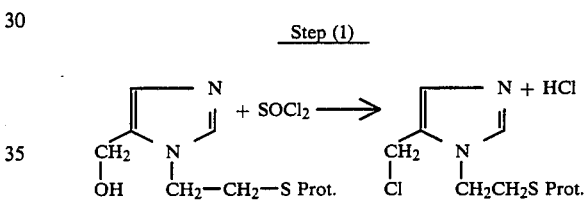

wherein Prot. is a sulfur protecting group.

Step (2)

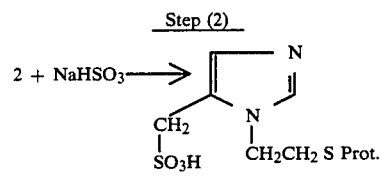

Step (3)

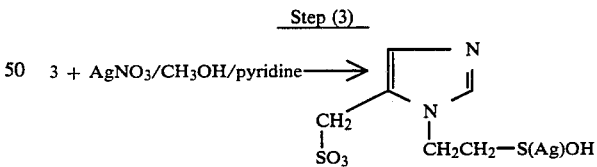

Step (4)

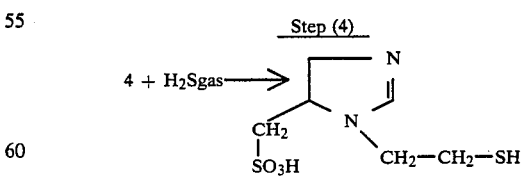

In step (1) the hydroxy is replaced by a halogen with thionyl chloride in an organic solvent to form compounds 2.

In step (2) the sulfonic acid (compound 3) is obtained by reacting compound 2 with an excess (about 2-3 equivalents) of sodium acid sulfate in aqueous solution.

In step (3) the sulfur protecting group is removed by reaction with silver nitrate and methanol in pyridine to obtain the silver salt compound 4.

Immediately upon completion of step (3), step (4) is conducted by reacting hydrogen sulfide gas with compound 4 to obtain the free thiol which is a compound within the scope of formula L. Reaction of compound L with ½ equivalent of the sulfoxide K obtains the carboxyl protected compound XIII.

Deprotection is accomplished as described for step (i) of Process A to obtain compounds of formula I.

Using other heterocyclic compounds analogous to compounds L wherein L" is —SO₃H and following the above reaction schemes gives the analogous compounds of formula I. Examples of typical, representative suitable starting materials are the following.

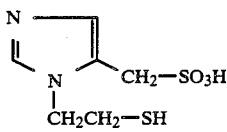

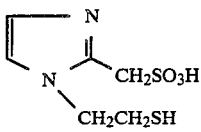

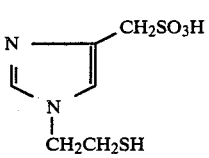

Compounds within the scope of compound L wherein L" is —COOH are prepared as shown in scheme VII

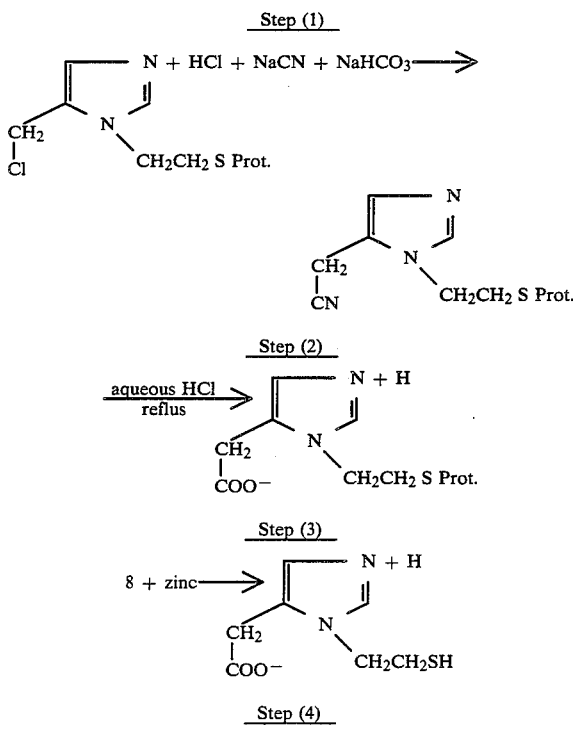

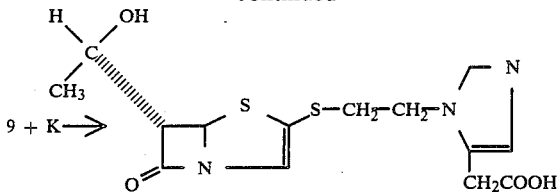

In step (1), the chloro is replaced by a cyano group by reacting about 2.1 equivalents of NaCN and 1 equivalent of NaHCO₃ in aqueous THF for about 5 minutes to obtain compound 7.

In step (2), compound 7 is refluxed with aqueous HCl (30%) to obtain compound 8.

In step (3), compound 8 is reacted with zinc dust to remove the sulfur protecting group, e.g. trityl, to obtain the thiol 9.

In step (4), compound 9 is reacted with the sulfoxide K to obtain the carboxyl protected compound 10 which is a compound of formula XII.

Deprotection is accomplished as described for step (i) of Process A to obtain compounds of formula I.

Using other heterocyclic compounds analogous to compounds L wherein L" is —COOH and following the above reaction schemes gives the analogous compounds of formula I. Examples of typical, representative suitable starting materials are the following

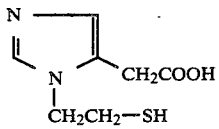

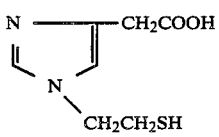

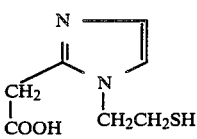

The following examples illustrate the preparation of the compounds and compositions of this invention.

EXAMPLE 1

Preparation of allyl 4-chloromethylimidazol-1-yl acetate HCl

A. Preparation of allyl-4-hydroxymethylimidazol-1-yl acetate and allyl-5-hydroxymethylimidazol-1-yl acetate React a solution of 4(5) hydroxymethyl imidazole (980 mg) in dry DMF (30 ml) with allyl iodoacetate (2.7 g) in the presence of powdered potassium hydroxide (580 mg) at ice bath temperature for 1 hour. Treat the resulting solution with CO₂ to quench excess hydroxide. Remove DMF (dimethyl formamide) under vacuum. Separate the products, allyl-4-hydroxymethylimidazol-1-yl acetate and allyl-5-hydroxymethylimidazol-1-yl acetate on a silica gel column using 5% MeOH/CH₂Cl₂.

B. Preparation of allyl-4-chloromethyl-imidazol-1-yl acetate Hydrochloride

React allyl-4-hydroxymethylimidazol-1-yl acetate with excess thionyl chloride in $CH_2Cl_2$ at ice bath temperatures for about 8 hours to form the title compounds.

EXAMPLE 2

Preparation of allyl (5R,6S,8R)-2-thiol-6-(1-hydroxyethyl)penem-3-carboxylate and allyl (5R,6S,8R)-2-thiocarbonyl-6-(1-hydroxyethyl)penem-3-carboxylate

(A) Preparation of (3S,4R)-1-allyloxycarbonylmethyl)-3-(1-hydroxyethyl)-4-(triphenylmethylthio)azetidin-2-one Add 0.3 gm of (3S,4R)-3-(1-hydroxyethyl)-4-(triphenylmethylthio)azetidin-2-one to 10 ml of acetonitrile containing 0.286 gm of cesium carbonate. Add 0.2 gm of a-iodo allyl acetate to the system. Stir the system at room temperature for 16 hours. Dilute with ether (50 ml), filter and wash the ether layer with 1% aqueous phosphoric acid, followed by water. After drying over sodium sulfate remove solvent to give a foamy solid.

(B) Preparation of (3S,4R)-3-(1-hydroxyethyl)-1-allyloxycarbonylmethyl-4-sulfhydryl-azetidin-2-one Add 500 mg of (3S,4R)-1-allyloxycarbonylmethyl)-3-(1-hydroxyethyl)-4-(triphenylmethylthio)azetidin-2-one and 20 ml tetrahydrofuran to a 50 ml flask. Add zinc dust and 10% hydrochloric acid in small portions over 1 hour until all of the starting material is reacted. Recover the product by filtering off the excess zinc and removing the solvent to crystallize the title product.

NMR: $(CDCl_3)$=6.2–5.7(1H, m); 5.5–5.15 (2H, m); 5.0 (1H, dd, J=3,9 c/s); 4.75–4.55 (2H, m); 4.45–3.95 (1H, m); 4.14(1H, d, J=18 c/s); 3.78(1H, d, J=18 c/s); 3.19(1H, dd, J=6,3 c/s); 2.09(1H, d, J=9 c/s); 1.34 (3H, d, J=6 c/s).

(C) Preparation of (3S,4R)-3-(1-trimethylsilyloxy-ethyl-1-allyloxycarbonylmethyl-4-sulfhydryl-azetidin-2-one Add the entire amount of (3S,4R)-3-(1-hydroxyethyl)-1-allyloxycarbonylmethyl-4-sulfhydryl-azetidin-2-one produced in step (B) above to 25 ml of methylene chloride. To this system add 1.1 ml of bis silylacetamide. Stir the system at room temperature for 15 minutes to give the title compound.

(D) Preparation of (3S,4R)-1-(allyloxycarbonylmethyl)-3-(1-trimethyl-silyloxyethyl)-4-(1'-imidazolylthiocarbonylthio)azetidin-2-one After completion of step (C) above and to the same solution add 350 mg of thiocarbonyldiimidazole. Stir the system at room temperature for 3 hours. Filter the solution and wash the precipitate with methylene chloride. Collect the filtrate and remove the methylene chloride by stripping. Chromatograph the residue on silica gel eluting with 20% ethyl acetate/methylene chloride to yield 335 mg of the title compound.

NMR:=8.4, 1H, s; 7.65, 1H, d(J=1 Hz); 7.05, 1H (dJ=1 Hz); 5.95, 1H, d (J=2 Hz); 5.8; 1H, m; 5.45–5.1, 2H, m; 4.3, 1H, m; 4.1, 2H, Q(J=16 Hz); 3.5, d d (J=2,6); 1.35; 3H, d (J=6 Hz).

(E) Preparation of (5R,6S,8R) allyl-2-thiol-6-(1-trimethylsilyloxyethyl)penem-3-carboxylate and (5R,6S,8R) allyl-2-thiocarbonyl-6-(1-trimethylsilyloxyethyl)penam-3-carboxylate Add 170 mg of (3S,4R)-1-(allyloxycarbonylmethyl)-3-(1-trimethylsilyloxyethyl)-4-(1'-imidazolylthiocarbonylthio)azetidin-2-one to 40 ml of anhydrous tetrahydrofuran under a nitrogen atmosphere. Cool the system to −78° C. and then add 0.6 ml of 1M lithium di-(trimethylsilyl)amine in hexane dropwise to the system. Stir the system at −78° C. for 5 minutes. Add 0.2 ml of acetic acid to the system. Dilute the system to 200 ml with methylene chloride. Wash the organic solution with water, aqueous sodium bicarbonate solution and again with water. Purify the product by chromatography by rapidly eluting the sample through silica gel with 5% ethyl acetate/methylene chloride to afford 125 mg of the desired products and the desilylated products.

(F) Preparation of (5R,6S,8R) Allyl-2-thiol-6-(1-hydroxyethyl)penem-3-carboxylate and (5R,6S,8R) Allyl-2-thiocarbonyl-6-(1-hydroxyethyl)penam To a 25 ml flask add the entire mixture produced in step (E) along with 5 ml of tetrahydrofuran, 1 ml of water and 1 ml of acetic acid. Stir the system at room temperature for 2 hours. Add ethyl acetate to the solution and wash the organic phase with sodium bicarbonate solution, water and then brine. Dry the organic phase over anhydrous sodium sulfate, filter and remove the solvent by stripping to give the title compound.

EXAMPLE 3

(5R,6S,8R)2-(1-carboxymethyl-4-imidazolylmethylthio)-6-(1-hydroxyethyl)penem-3-carboxylic acid

(A) Preparation of Allyl(5R,6S,8R)-2-(carboxymethyl-4-imidazolylmethylthio)-6-(1-hydroxyethyl)penem-3-carboxylate To a solution of 0.5 g of the thione prepared in Example 2 in 10 ml tetrahydroduran (THF), add 0.5 g allyl-4-chloromethyl-imidazol-1-yl acetate hydrochloride, followed by 2.0 ml of a 5% sodium bicarbonate solution, and stir at room temperature for 3 hours or until thin layer chromatography (ethyl acetate/THF, 50/50) indicates no starting material is left. Evaporate the THF in vacuo, add 10 ml water to the resultant residue and extract with 2×20 ml methylene chloride. Dry the organic layer over sodium sulfate and concentrate in vacuo to an oil. Purify the crude oil by column chromatography (silica gel, eluted with 5% methanol in methylene chloride) to obtain 400 mg of the title compound of Step A.

(B) Preparation of (5R,6S,8R)-2-(1-carboxymethyl-4-imidazolyl-methylthio)-6-(1-hydroxyethyl)penem-3-carboxylic acid Under argon, add 100 mg of the allyl ester of Step A to 10 ml methylene chloride, followed by 25 mg triphenyl phosphine, 45 ml 2-ethyl hexanoic acid, and 10 mg Pd° reagent. Let stand until the reaction is complete as shown by thin layer chromatography (5% methanol in methylene chloride as solvent). Extract the resultant product with 2×10 ml water, then wash the aqueous layer with 3×10 ml methylene chloride. Lyophilize the aqueous layer to obtain the title compound.

Purify the product by reverse phase column chromatography (25 g silica gel eluted with water) to obtain the title compound.

EXAMPLE 4

Preparation of allyl-5-chloromethyl-imidazol-1-yl acetate hydrochloride

React allyl-5-hydroxymethylimidazol-1-yl acetate with excess thionyl chloride in $CH_2Cl_2$ at ice bath temperatures for about 8 hours to form the title compound.

EXAMPLE 5

5R,6S,8R-2-(carboxymethyl-5-imidazolylmethylthio)-6-(1-hydroxyethyl)penem carboxylic acid (A) Preparation of Allyl(5R,6S,8R)-2-(1-carboxymethyl-5-imidazolylmethylthio)-6-(1-hydroxyethyl)penem-3-carboxylate To a solution of 0.5 g of the thione prepared in Example 2 in 10 ml tetrahydrofuran (THF), add 0.5 g allyl-5-chloromethyl-imidazol-1-yl acetate hydrochloride, followed by 2.0 ml of a 5% sodium bicarbonate solution, and stir at room temperature for 3 hours or until thin layer chromatography (ethyl acetate/THF, 50/50) indicates no starting material is left. Evaporate the THF in vacuo, add 10 ml water to the resultant residue and extract with 2×20 ml methylene chloride. Dry the organic layer over sodium sulfate and concentrate in vacuo to an oil. Purify the crude oil by column chromatography (silica gel, eluted with 5% methanol in methylene chloride) to obtain 100 ml of the title compound of Step A.

(B) Preparation of 5R,6S,8R-2-(1-carboxymethyl-5-imidazolylmethylthio)-6-(1-hydroxyethyl)penem carboxylic acid Under argon, add 100 mg of the allyl ester of Step A to 10 ml methylene chloride, followed by 25 mg triphenyl phosphine, 45 ml 2-ethyl hexanoic acid, and 10 mg Pd° reagent. Let stand until the reaction is complete as shown by thin layer chromatography (5% methanol in methylene chloride as solvent). Extract the resultant product with 2×10 ml water, then wash the aqueous layer with 3×10 ml methylene chloride. Lyophilize the aqueous layer to obtain the title compound.

Purify the product by reverse phase column chromatography (25 g silica gel eluted with water) to obtain the title compound.

EXAMPLE 6

Preparation of 5-chloromethyl imidazol-4-yl methane sulfonic acid (A) Preparation of 4,5 di(hydroxymethyl)imidazole Reflux dimethyl 4,5 imidazole dicarboxylate (1.8 g) in THF (tetrahydrofuran) with 2.5 equivalents of LAH lithium aluminum hydride). Neutralize with NH4Cl solution and filter. Concentrate the filtrate under vacumm and extract the product with ethanol. Remove the solvent, filtrate through alumina using a THF solvent to give the title compound.

(B) Preparation of 4,5 di(chloromethyl)imidazole

Suspend the product of A in $CH_2Cl_2$ cooled to the temperature of an ice bath. Add excess thionyl chloride and stir overnight to obtain the title compound.

(C) Preparation of 5-chloromethyl imidazol-4-yl · methane sulfonic acid

Stir the product of B with one equivalent of $Na_2SO_3$ in dimethyl formamide (DMF) to yield the title compound.

EXAMPLE 7

Preparation of 5R,6S,8R-2-(4-sulfonic acid methyl-5-imidazolylmethylthio)-6-(1-hydroxymethyl)-penem-3-carboxylic acid (A) Preparation of allyl-(5R,6S,8R)-2-(4-sulfonic acid methyl-5-imidazolylmethylthio)-6-(1-hydroxymethyl)-penem-3-carboxylate Dissolve the triethyl amine salt of the thione prepared in Example 2 in the final reaction mixture of Example 6C at ice bath temperature. Isolate the product from a reverse phase column using 20% acetonitrile-water as the eluant.

(B) Preparation of 5R,6S,8R-2-(4-sulfonic acid methyl-5-imidazolylmethylthio)-6-(1-hydroxymethyl)-penem-3-carboxylic acid Follow the procedure of Example 3B to prepare the title compound by deprotecting the carboxylic acid group.

EXAMPLE 8

Allyl-(5R,6S,8R,2'RS)-2-(ethanesulfinyl-6-(1-hydroxyethyl)penem-3-carboxylate

Stir a solution of allyl-(5R,6S,8R,2'RS)-2-(ethanethio)-6-(1-hydroxyethyl)penem-3-carboxylate (31.5 g) in ethyl acetate (200 ml) and dichloromethane (100 ml) at 0°–5° C. Add a solution of m-chloroperoxybenzoic acid (80–85%; 22 g) in ethyl acetate (120 ml) over 0.5 hour. After a further 0.5 hour, add the the solution to a stirred mixture of ethyl acetate (150 ml), water (125 ml) and sodium bicarbonate (15 g) and stir rapidly for 15 minutes. Dry the organic phase over $MgSO_4$, evaporate and chromatograph rapidly on silica gel, eluting 1:1 hexane-ethyl acetate then pure ethyl acetate. Evaporate the product fractions and pump the residue at high vacuum to give the title compound as a thick yellow oil.

NMR(CDCl$_3$): δ1.2–1.6 (m, 6H), 3.0–3.35 (m, 2H), 3.38 (br.s, 1H, exch by D$_2$O), 3.83 (m, 1H), 4.18 (m, 1H), 4.75 (br.d, J=6.5 Hz), 5.2–5.6 (m, 2H), 5.73 and 5.89 (both d, J-1.5 Hz, total 1H) and 5.8–6.2 (m, 1H).

The compound obtained is a mixture of isomers diastereoisomeric at the oxidized sulfur. The mixture was used as such in the next step since both isomers react.

EXAMPLE 9

Preparation of 1-(1-[2-triphenylmethylthio]ethyl)-4-hydroxymethyl imidazole

A. To a flask containing 4 gms 4-hydroxymethyl imidazole hydrochloride in 30 ml dimethylformamide add 3.1 ml vinylethyl ether and 50 mg paratoluene sulfonic acid. Stir for 1½ hours until the reaction is complete. Extract from saturated $K_2CO_3$/NaCl with ethylacetate to obtain 1-ethoxy-1-(imidazol-4-yl)methoxy ethane.

B. Heat the product of step A of this Example 9 with 5.2 g ethylene carbonate in an oil bath at 125° C. for about 2 hours. Elute on a coarse silica column with $CH_2Cl_2$ then 3% $CH_3CH_2OH/CH_2Cl_2$ then 5%

CH₃CH₂OH/CH₂Cl₂ to obtain 2 of 1-ethoxy-1-(N-hydroxyethylimidazol-4- or 5-yl)methoxy ethane.

C. Add dry CH₂Cl₂ to the first fraction of Step B of this Example 9 and cool to 0° C. Add 1.07 ml triethyl amine and 0.54 ml of CH₃SO₂Cl and stir for ½ hour to complete the reaction and obtain 1-ethoxy-1-(N-chloroethyl(imidazol-4-yl)methoxy ethane.

D. Add dry CH₂Cl₂ to 1.16 gm of the second fraction obtained in Step B of this Example 9 and cool to 0° C. Add 0.9 ml triethylamine and 0.45 ml CH₃SO₂Cl and stir for ½ hour to complete the reaction and obtain 1-ethoxy-1-(N-chloroethyl(imidazol-5-yl)methoxy ethane.

E. Add 30 ml THF to 300 mg KOH and stir until dissolved. Add 1 gm trityl thiol and 970 mg of the second fraction obtained in step D of this Example 9 and stir for 15 minutes. Add CH₂Cl₂ and wash with water. Dry over Na₂SO₄ to obtain 1-ethoxy-1-(N-[2-triphenylmethylthio]ethyl)-4-hydroxy methyl imidazole.

F. Add 1.56 gm of the product of step E of this Example 9, 25 ml THF, 5 ml water and 630 mg of paratoluene sulfonic acid and stir for about 2 hrs. Add 280 mg NaHCO₃ and stir 10 mins. at pH about 7. Add 50 mg more NaHCO₃ and stir 10 minutes. Remove the solvent and add CH₂Cl₂. Separate the product in the organic layer. Remove the solvent to obtain the title compound.

The compound prepared in Example 9 is reacted as described in reaction schemes VI and VII to obtain the compounds of formula I wherein the heterocyclic moiety is bonded to the penem through a ring nitrogen.

Following the procedures of the preceding examples using the appropriate starting materials the following compounds are made:

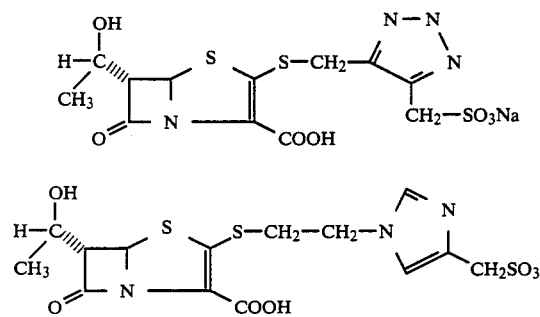

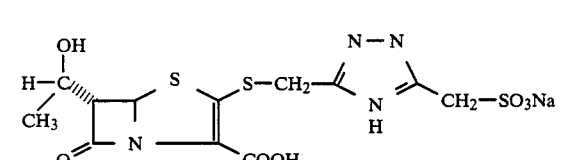

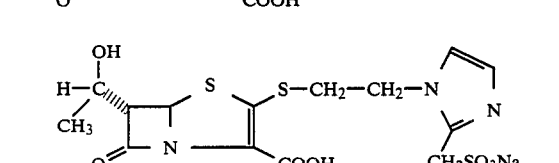

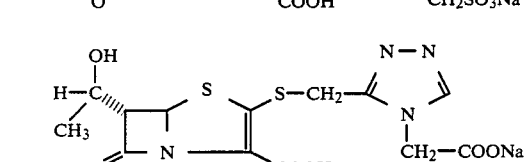

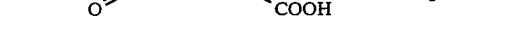

-continued

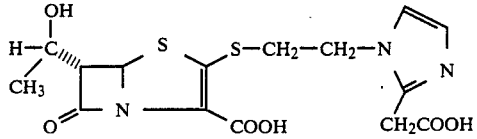

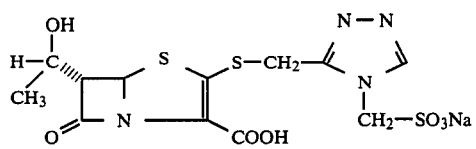

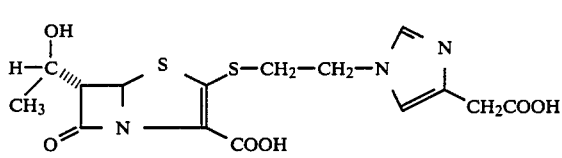

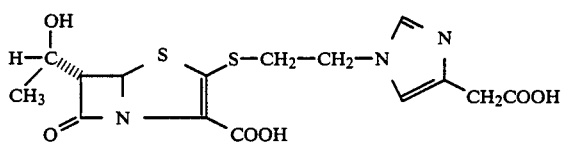

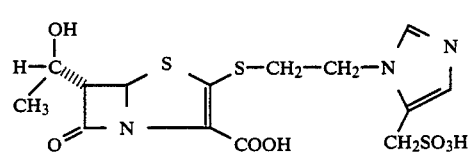

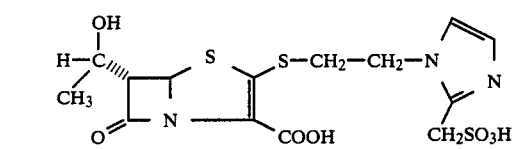

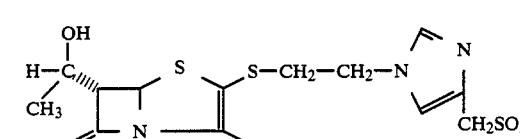

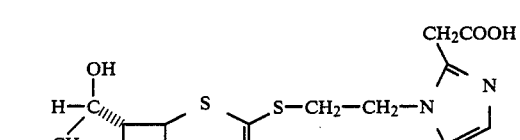

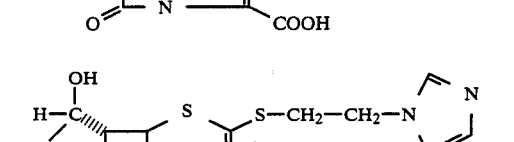

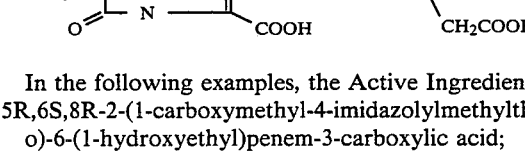

In the following examples, the Active Ingredient is 5R,6S,8R-2-(1-carboxymethyl-4-imidazolylmethylthio)-6-(1-hydroxyethyl)penem-3-carboxylic acid; 5R,6S,8R-2-(1-carboxymethyl-5-imidazolylmethylthio)-6-(1-hydroxyethyl)penem-3-carboxylic acid; or 5R,6S,8R-2-(4-sulfonic acid methyl-5-imidazolylmethylthio)-6-(1-hydroxyethyl)penem-3-carboxylic acid; or an equivalent amount of a penem of a compound of formula I.

EXAMPLE 10

| | Capsules | | |
|---|---|---|---|
| No. | Ingredient | mg/capsule | mg/capsule |
| 1. | Active ingredient | 250 | 500 |
| 2. | Lactose USP | 100 | 50 |
| 3. | Corn Starch, Food Grade | 50 | 43.5 |
| 4. | Microcrystalline Cellulose NF | 95 | 50 |
| 5. | Magnesium Stearate NF | 5 | 6.5 |
| | Total | 500 | 650 |

Method of Manufacture

Mix Items Nos. 1, 2, 3 and 4 in a suitable mixer for 10–15 minutes. Add Item No. 5 and mix for 1–3 minutes. Fill the mixture into suitable two-piece hard gelatin capsules using encapsulating machine.

EXAMPLE 11

| | Tablets | | |
|---|---|---|---|
| No. | Ingredient | mg/tablet | mg/tablet |
| 1. | Active ingredient | 250 | 500 |
| 2. | Lactose USP | 57 | 114 |
| 3. | Corn Starch, Food Grade, as a 10% paste in Purified Water | 20 | 40 |
| 4. | Corn Starch, Food Grade | 18 | 39 |
| 5. | Magnesium Stearate NF | 5 | 7 |
| | Total | 350 | 700 |

Method of Manufacture

Mix Item Nos. 1 and 2 in a suitable mixer for 10–15 minutes. Granulate the mixture with Item No. 3. Pass the wet granulation through a coarse screen (e.g., ¼″) if needed, and dry the wet granules. Mill the dried granules. Combine Item No. 4 and the dried granules and mix for 10–15 minutes. Add Item No. 5 and mix for 1–3 minutes. Compress the mixture to appropriate size and weight on a suitable tablet machine.

EXAMPLE 12

| Injectable Powder: (per vial) | | |
|---|---|---|
| | g/vial | g/vial |
| Active Ingredient | 0.5 | 1.0 |

Add sterile water for injection or bacteriostatic water for injection for reconstitution.

EXAMPLE 13

| Injectable Solution | | |
|---|---|---|
| Ingredient | mg/ml | mg/ml |
| Active Ingredient | 100 | 500 |
| Methylparaben | 1.8 | 1.8 |
| Propylparaben | 0.2 | 0.2 |
| Sodium Bisulfite | 3.2 | 3.2 |
| Disodium Edetate | 0.1 | 0.1 |
| Sodium Sulfate | 2.6 | 2.6 |
| Water for Injection q.s. ad | 1.0 ml | 1.0 ml |

Method of Manufacture

1. Dissolve parabens in a portion (85% of the final volume) of the water for injection at 65°–70° C.
2. Cool to 25.35° C. Charge and dissolve the sodium bisulfite, disodium edetate and sodium sulfate.
3. Charge and dissolve the active ingredient.
4. Bring the solution to final volume by adding water for injection.
5. Filter the solution through 0.22 micron membrane and fill into appropriate containers.
6. Terminally sterilize the units by autoclaving.

EXAMPLE 14

| Injectable Powder: (per vial) | |
|---|---|
| | g/vial |
| Active Ingredient | 1.0 |
| Sodium Citrate | 0.05 |

PH is adjusted to 6.2 using 0.1N citric acid solution.

Add sterile water for injection or bacteriostatic water for injection for reconstitution.

We claim:

1. Compounds represented by the formula

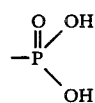

and pharmaceutically acceptable salts and esters thereof in racemic or optically active forms wherein n is 1, 2 or 3; m is 1, 2 or 3;

Z represents —COOH, —SO$_3$H, $$-\underset{\underset{OH}{\overset{O}{\|}}}{P}\diagdown_{OH}$$

or alkali metal salts thereof;

R, R$_1$, R$_2$ and R$_3$ independently represent hydrogen, lower alkyl, hydroxy lower alkyl, amino lower alkyl, carboxy lower alkyl, thio lower alkyl, lower alkoxy lower alkyl, carbonylamino lower alkyl, aminocarbonyl lower alkyl, cyano lower alkyl, fluoro lower alkyl, carbamoyloxy lower alkyl, or sulfamoyloxy with the proviso that when m is 2 or 3, R, R$_1$, R$_2$ and R$_3$ independently additionally represent hydroxy, amino, cyano, fluoro, carbamoyloxy, carbonylamino or —SO$_3$H;

each X independently represents —CH—, —N—, —S— or —O— with the proviso that at least one X is —N—.

2. Compounds of claim 1 wherein n is 1 or 2, m is 1, R, R$_1$, R$_2$ and R$_3$ are independently hydrogen or lower alkyl; Z is —SO$_3$H or —COOH and two non-adjacent X's are —N—.

3. Compounds of claim 1 wherein n is 1, m is 1, R$_1$ and R$_3$ ore each hydrogen, R and R$_2$ are independently hydrogen or lower alkyl, Z is —SO$_3$H and the heterocyclic ring is 2-imidazole.

4. A compound of claim 1 which is 5R,6S,8R-2-(1-carboxymethyl-4-imidazolylmethylthio)-6-(1-hydroxyethyl)penem-3-carboxylic acid.

5. A compound of claim 1 which is 5R,6S,8R-2-(carboxymethyl-5-imidazolylmethylthio)-6-(1-hydroxyethyl)penem carboxylic acid.

6. A compound of claim 1 which is 5R,6S,8R-2-(4-sulfonic acid methyl-5-imidazolylmethylthio)-6-(1-hydroxymethyl)penem-3-carboxylic acid.

7. A pharmaceutical composition comprising an antibacterial effective amount of a compound of claim 1 in admixture with a pharmaceutically acceptable carrier therefor.

8. A composition according to claim 7 wherein said antibacterial compound is 5R,6S,8R-2-(1-carboxymethyl-4-imidazoyl-methylthio)-6-(1-hydroxyethyl)penem-3-carboxylic acid.

9. A composition according to claim 7 wherein said antibacterial compound is 5R,6S,8R-2-(carboxymethyl-5-imidazolylmethylthio)-6-(1-hydroxyethyl)penem carboxylic acid.

10. A composition according to claim 7 wherein said antibacterial compound is 5R,6S,8R-2-(4-sulfonic acid methyl-5-imidazolylmethylthio)-6-(1-hydroxymethyl)-penem-3-carboxylic acid.

11. A method of preventing bacterial infections in warm blooded animals in need of such treatment which comprises administering an antibacterial effective amount of a compound of claim 1.

12. The method of claim 11 wherein the compound administered is 5R,6S,8R-2-(1-carboxymethyl-4-imidazolylmethylthio)-6-(1-hydroxymethyl)penem-3-carboxylic acid.

13. The method of claim 11 wherein the compound administered is bacterial compound is 5R,6S,8R-2-(carboxymethyl-5-imidazolylmethylthio)-6-(1-hydroxyethyl)penem carboxylic acid.

14. The method of claim 11 wherein the compound administered is 5R,6S,8R-2-(4-sulfonic acid methyl-5-imidazolylmethylthio)-6-hydroxymethyl)penem-3-carboxylic acid.

* * * * *